United States Patent [19]
Berke et al.

[11] Patent Number: 6,048,345
[45] Date of Patent: Apr. 11, 2000

[54] MOTORIZED RECIPROCATING SURGICAL FILE APPARATUS AND METHOD

[75] Inventors: Joseph J. Berke, 3248 Interlaken, West Bloomfield, Mich. 48323; Charles T. Michael, Troy, Mich.

[73] Assignee: Joseph J. Berke, West Bloomfield, Mich.

[21] Appl. No.: 09/288,161

[22] Filed: Apr. 8, 1999

[51] Int. Cl.[7] .................................................. A61B 17/00
[52] U.S. Cl. ............................ 606/85; 606/171; 606/177
[58] Field of Search ........................... 606/85, 171, 177; 30/392, 394

[56] References Cited

U.S. PATENT DOCUMENTS

| | | |
|---|---|---|
| 4,203,444 | 5/1980 | Bonnell et al. . |
| 4,589,414 | 5/1986 | Yoshida et al. . |
| 4,601,290 | 7/1986 | Effron et al. . |
| 4,985,031 | 1/1991 | Buss et al. . |
| 5,387,215 | 2/1995 | Fisher . |
| 5,940,977 | 8/1999 | Moores, Jr. ............................ 30/392 |

Primary Examiner—Michael Buiz
Assistant Examiner—Julian W. Woo
Attorney, Agent, or Firm—Alex Rhodes

[57] ABSTRACT

A motor driven reciprocating surgical file apparatus and method for trimming and shaping hard body materials. A small file is detachably mounted on the distal end of a reciprocating offset arm. The offset arm allows the file to be inserted and manipulated in a surgical site. The file is comprised of a slender elongated upward extending arm and an adjoining lower file portion. A plurality of teeth surround the file portion and are arranged to shape and trim bone and cartilage in a direction which is substantially parallel to the reciprocating motion of a motor's output shaft. A coupling is provided on the reciprocating arm for detachably mounting optional files. A control circuit allows a surgeon to vary the rate at which the file reciprocates. In a first aspect of the invention, the reciprocating file is driven by a battery operated electric motor. In a second aspect of the invention, the reciprocating arm is driven by an AC motor. In both aspects of the invention, a plurality of files with optional shapes and tooth arrangements are provided.

24 Claims, 6 Drawing Sheets

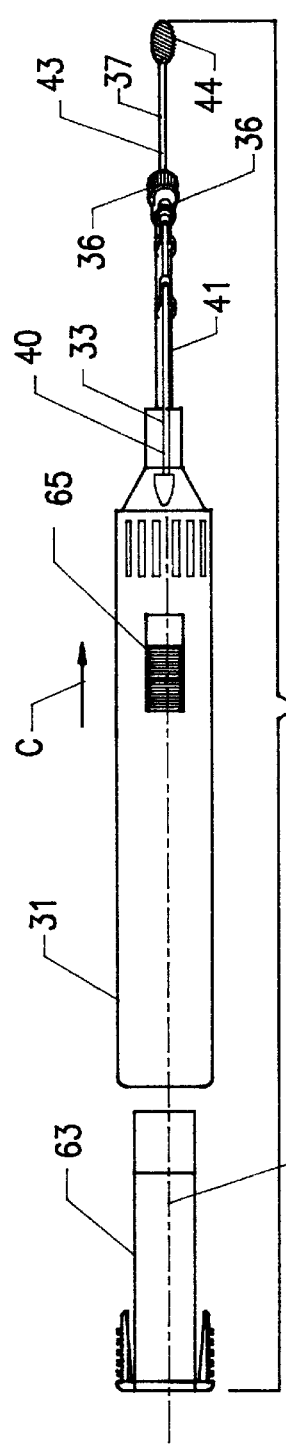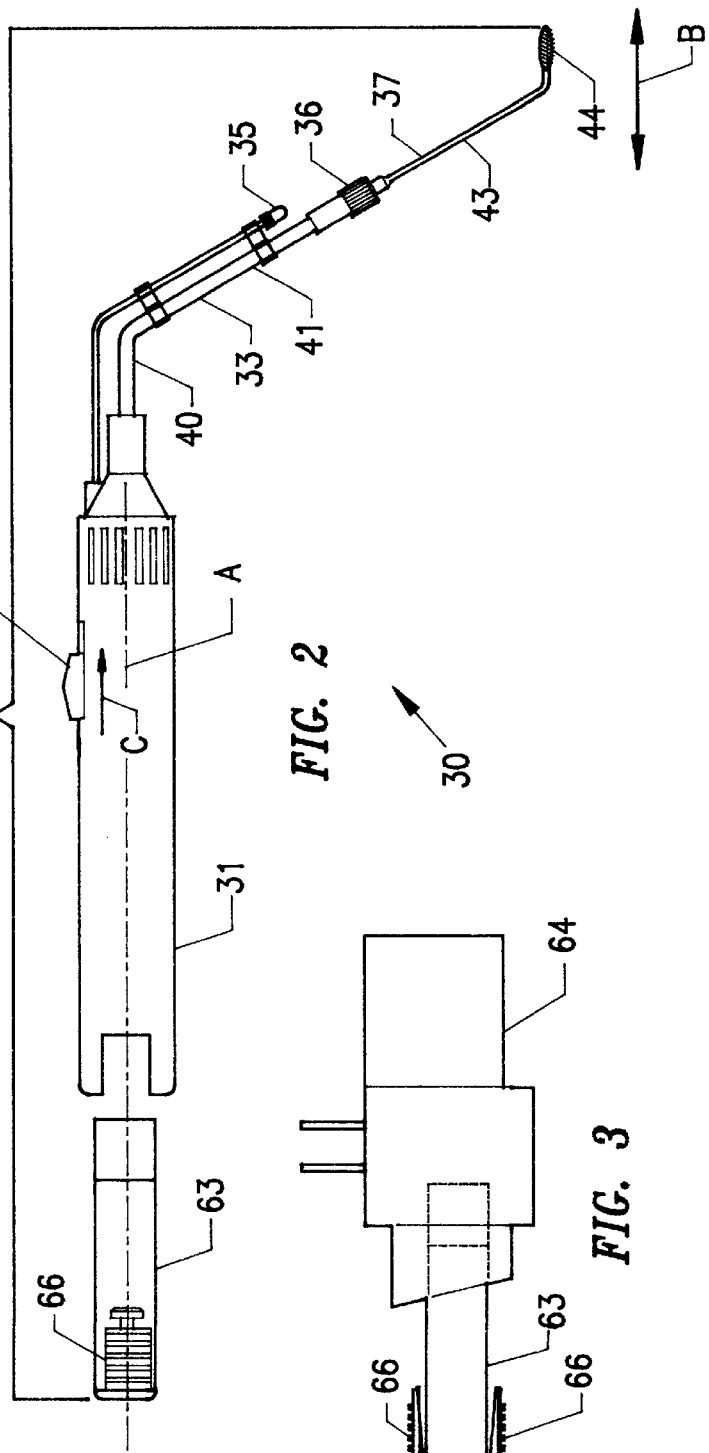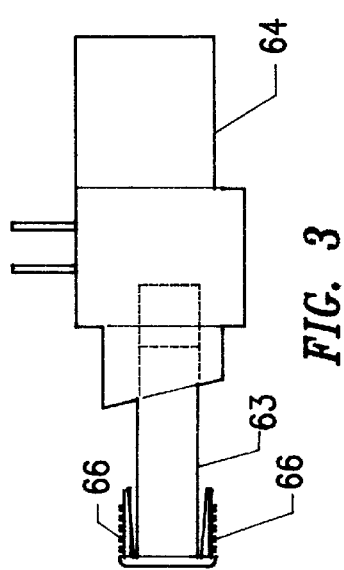

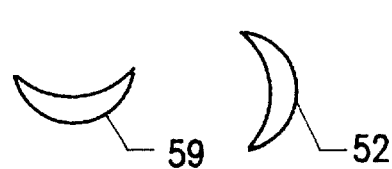 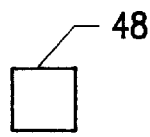 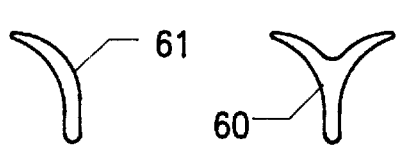
FIG. 20  FIG. 21  FIG. 22  FIG. 23  FIG. 24
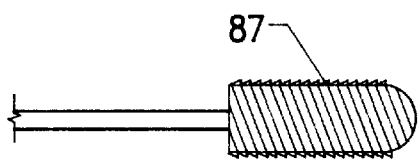 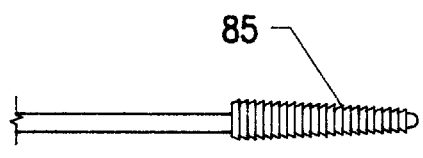
FIG. 27  FIG. 25
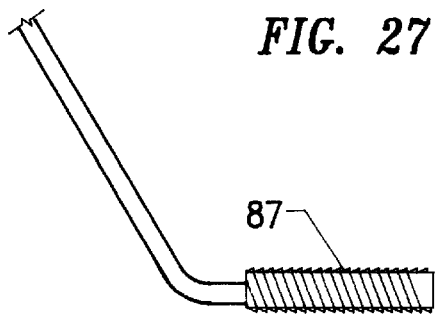 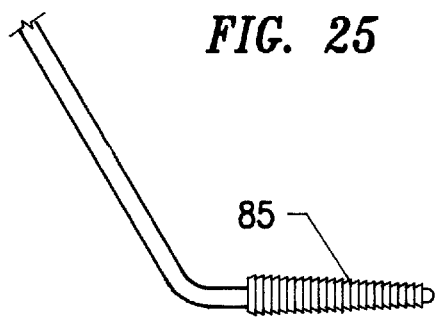
FIG. 28  FIG. 26
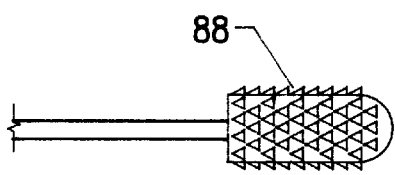 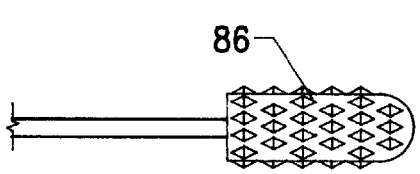
FIG. 31  FIG. 29
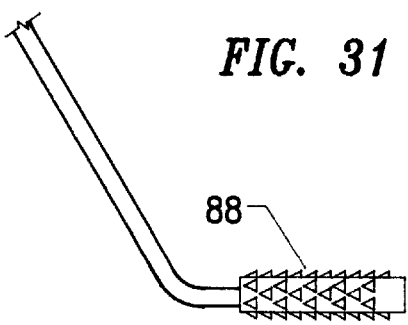 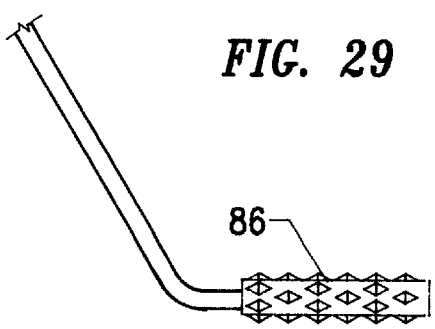
FIG. 32  FIG. 30

MOTORIZED RECIPROCATING SURGICAL FILE APPARATUS AND METHOD

FIELD OF THE INVENTION

This invention is related to surgical bone and cartilage trimming and shaping instruments and more particularly to a motor driven reciprocating surgical file apparatus and method.

BACKGROUND OF THE INVENTION

Numerous surgical scalpels, knives, saws, burrs, drills, files, and gouges exist in the art for cutting, shaping, trimming and removing hard materials such as bone, cartilage, and calcification during orthopedic, reconstructive, and neurosurgical procedures. The numerous surgical cutting, trimming and shaping instruments add to the complexity and increase the time for performing surgery.

U.S. Pat. Nos. 4,203,444; 4,589,414; 4,601,290; and 5,387,215 are exemplary of power operated surgical files in the prior art. One characteristic which is common to each of these patents is that a rotary or reciprocating file is aligned with an axis of a motor. One drawback of this construction is that its uses are limited to certain surgical procedures and sites. By way of example, U.S. Pat. No. 4,601,290 is directed to performing joint surgery such as knee surgery utilizing surgical viewing probes inserted through punctures. Another drawback is that it has limited mobility in a surgical site. Another drawback is that its ability at a surgical site is limited for trimming and shaping hard body materials.

SUMMARY OF THE INVENTION

Modern surgical techniques and especially reconstructive surgical bone and joint procedures require new and appropriate surgical instruments and methods. A small motor driven reciprocating file mounted on an offset arm provides an appropriate tool and method for shaping and trimming hard body materials. The motor driven offset file will provide maximum mobility and enhance the development and performance of improved surgical techniques, especially in areas with limited exposure or in confined anatomical locations. Intracranial, intra and transnasal procedures, knee, shoulder and hip reconstructions as well as many orthopedic, podiatric and neurosurgical operations will be facilitated and engendered by the present invention.

Other specific surgical uses will include the smoothing of roughened surfaces of cranial bones and lamina after use of a craniotome, rongeur or curette. This invention allows enlargements of bony foramina, creating unhindered passage of nerves and blood vessels. Severe rheumatoid and osteoarthritic deformities of small bones of the hands and feet can be reshaped. Trimming of spurs, bunions and other exostoses or excrescences can be readily achieved. Better repair and improved function of damaged bones following fracture or dislocation are additional advantages as well. Not only the preparation of prosthetic recipient sites but also many prostheses made of elastomeric or other non-metallic materials can be fashioned for improved alignment and longevity of function. Reconstruction of bony articulations, tendon attachments and joint preservation are also benefits achievable with the use of this novel invention.

It is a primary object of the present invention to provide a small motorized surgical file which can be inserted into surgical sites for trimming and shaping hard materials, such as bones and cartilage, during procedures such as orthopedic and reconstructive surgery. It is another object, in addition to the foregoing object, to provide a power operated surgical file having a plurality of optional detachable files. It is another object, in addition to the foregoing objects, to reduce the complexity of surgical tools. It is another object, in addition to the foregoing objects, to reduce the time for performing surgery.

In accomplishing the foregoing objects, a small file is detachably mounted on the distal end of a reciprocating offset arm. The offset arm allows the file to be deeply inserted and manipulated in a surgical site. The file is comprised of a slender elongated upward extending arm and an adjoining lower file portion. A plurality of teeth which surround the file portion are arranged to shape and trim bone and cartilage in a direction which is substantially parallel to the reciprocating motion of a motor's output shaft.

One advantage of the offset arm is that the file can be inserted deeply into a surgical site. Another advantage of the offset arm is that a surgeon's view is not obstructed by the power source or the surgeon's hand. One advantage of the small file portion is that it can be easily manipulated at the surgical site.

In a first aspect of the invention, the reciprocating file is driven by a battery operated electric motor. A coupling is provided on the reciprocating arm for detachably mounting optional files. A control circuit allows the surgeon to vary the rate at which the file reciprocates. An illuminating means is mounted on the offset arm to illuminate the surgical site. In a second aspect of the invention, the reciprocating arm is driven by an AC motor. In both aspects of the invention, a plurality of files with optional shapes, sizes and teeth are provided. As used herein, the term "file" is intended to include devices having cutting ridges and raised points commonly referred to as files, rasps and burrs. The optional files which are described herein are designated in the usual manner by reference to their cross-sectional shapes, sizes and/or tooth patterns.

In employing the teaching of the present invention, a plurality of alternate constructions can be adopted to achieve the desired capabilities. In this disclosure, some alternate constructions are discussed. However, these embodiments are intended as examples, and should not be considered as limiting the scope of the invention.

Further features and benefits will become apparent by reference to the drawings and ensuing detailed description of a preferred embodiment which discloses the best mode contemplated in carrying out the invention. The exclusive rights which are claimed are set forth in each of the numbered claims following the detailed description of the preferred embodiment.

BRIEF DESCRIPTION OF THE DRAWINGS

The invention will be better understood and further objects, characterizing features, details and advantages thereof will appear more clearly with reference to the diagrammatic drawings illustrating specific embodiments of the invention by way of non-limiting example only.

FIG. 1 is an exploded plan view of a battery powered surgical file apparatus according to the present invention.

FIG. 2 is an exploded front view of the surgical file apparatus.

FIG. 3 is a front view of a battery charger.

FIG. 20 is an enlarged cross-section view of a concave-convex file.

FIG. 21 is an enlarged cross-section view of a second concave-convex file.

FIG. 22 is an enlarged cross-section view of a square file.

FIG. 23 is an enlarged cross-section view of an asymmetrical file.

FIG. 24 is an enlarged cross-section view of a "Y" file.

FIG. 25 is an enlarged partial plan view of a tapered file.

FIG. 26 is an enlarged partial front view of the tapered file.

FIG. 27 is an enlarged partial plan view of a rectangular fine file.

FIG. 28 is an enlarged partial front view of the rectangular fine file.

FIG. 29 is an enlarged partial plan view of a rectangular rasp file.

FIG. 30 is an enlarged partial front view of the rectangular rasp file.

FIG. 31 is an enlarged partial plan view of a second rectangular rasp file.

FIG. 32 is an enlarged partial front view of the second rectangular rasp file.

DETAILED DESCRIPTION OF A PREFERRED EMBODIMENT

Figure 4:
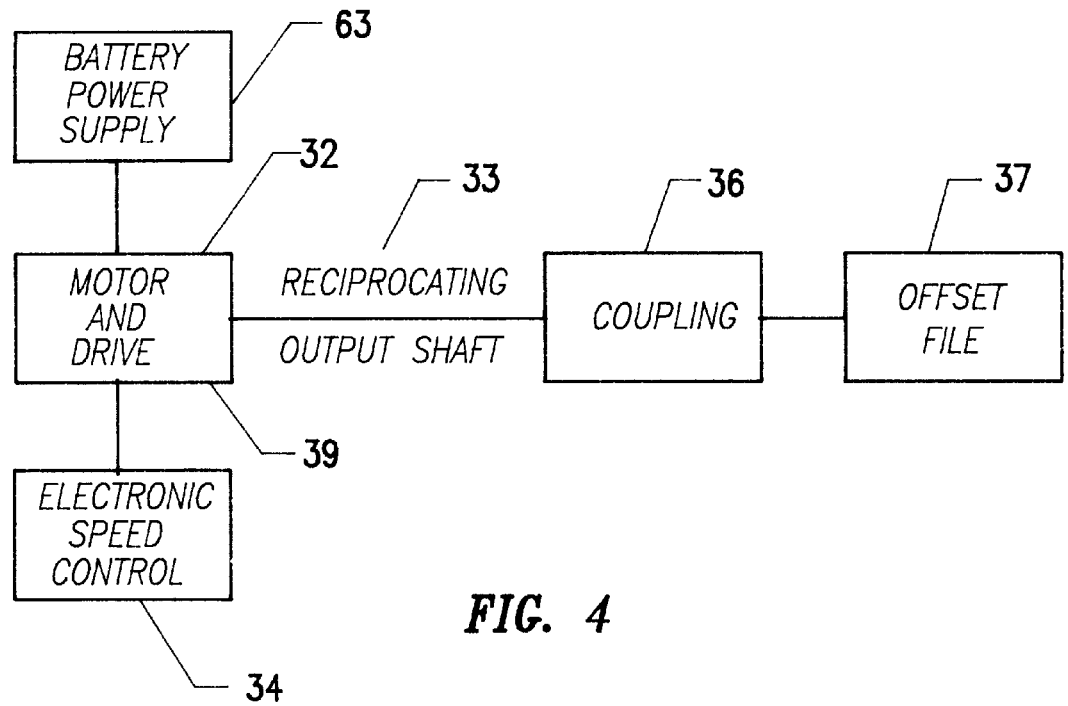
FIG. 4 is a block diagram of the surgical file apparatus.

Referring now to the drawings wherein like numerals designate like and similar parts throughout the several views, in FIGS. 1 through 4, a surgical file apparatus 30 is shown according to the present invention. The surgical file apparatus 30 is comprised of an elongated housing 31; a reciprocating means 32 having an output shaft 33; a control 34 for operating the power motive means 32; an illuminating means 35 for illuminating a surgical site; a coupling 36 for detachably mounting an offset file 37; and the detachable file 37. The reciprocating means 32 is a usual type small fractional horsepower electric motor and drive 39 or some other suitable means, such as a usual type solenoid drive (not shown). In the orientation used in the drawings, the reciprocating output shaft 33 is comprised of an upper portion 40 which is aligned with the rotational axis "A" of the motor 39 and an adjoining downward angular extending portion 41. The coupling 36 is attached to a lower end portion of the downward extending portion 41 of the reciprocating output shaft 33.

The file apparatus 30 is intended to be used for trimming and shaping hard body materials such as bones and cartilage, particularly during procedures such as endoscopic, orthopedic and reconstructive surgery (e.g. for removing and trimming portions of bones during orthopedic surgery). The offset file 37 has a slender upward extending arm portion 43 and an adjoining lower file portion 44. The lower file portion 44 reciprocates forwardly and rearwardly in a direction "B". A locating flat 45 is provided on an upper end portion of the offset file 37 to angularly position the offset file 37. The lower file portion 44 has a plurality of teeth 46 which cover the top, bottom, sides and most of the lower file portion 44. One primary feature of the invention is that the lower file portion 44 is substantially offset from the motor and drive 39. This allows the lower file portion 44 to inserted and manipulated within surgical sites more easily than existing shaping and trimming tools.

The variety of optional files is another important feature of the invention. The variety of optional files is a major advantage over rotary power cutters where only limited numbers of shapes are possible. Moreover, the optional files which conform to the contours of bones and cartilage will enhance the development and performance of improved surgical techniques.

Exemplary files are illustrated in cross-section in FIGS. 7 through 18. The files include regular polygons, such as the round file 47 of FIGS. 7–9 and the square file 48 of FIG. 22; files which are symmetrical with respect to a horizontal axis, such as the rectangular files 49, 50 of FIGS. 10 and 11, the half round file 51 of FIG. 15, the concave-convex file 52 of FIG. 21 and the "V-shaped" file 53 of FIG. 17; files which are symmetrical with respect to vertical axes, such as the half round files 54, 55 of FIGS. 13 and 14, the "V-shaped" file 56 of FIG. 16, the triangular files 57, 58 of FIGS. 18 and 19, the concave-convex file 59 of FIG. and the "Y-shaped" file 60 of FIG. 24; and the asymmetrical file 61 of FIG. 23; and inclined files, such as the rectangular file 62 of FIG. 12. In FIGS. 25 and 26 are shown a tapered file.

In FIGS. 27 through 32, inclusive, are shown files which are exemplary of optional tooth patterns. In FIGS. 27 and 28 an optional rectangular fine file 86 commonly referred to as a "mill" file is shown. In FIGS. 29 through 32 optional rectangular rasp files 87 and 88 are shown.

In the first aspect of the invention which is depicted in FIGS. 1 through 4, the power source of the surgical file apparatus is a battery 63 which is preferably replenished in a small charger 64 as shown in FIG. 3. On the top surface of the housing 31 is a slide control 65 for selectively changing the rate at which the offset file 37 reciprocates.

The rechargeable battery 63 is preferably retained in the housing 31 by a pair of flexible members 66 such that it can be recharged or quickly replaced with a fully charged spare battery 63. One advantage of the battery powered file apparatus 30 is its portability.

The motor and drive 39 is preferably a permanent magnet motor and drive to minimize size and weight. The motor's controls 34 include a speed control whereby the file's reciprocation rate can be selectively changed by advancing the slide control 65 in the direction of arrow "C". A variety of electronic controls are available for selectively controlling the speed of a small motor. The DC motor is known for the ease with which speed can be controlled by merely varying the voltage applied to the armature (assuming a permanent magnet motor). In the past, armature voltage has been varied with a rheostat. The shortcoming of this method, particularly with a battery power supply, is the power loss in the rheostat. A simple, more efficient alternative circuit is shown in schematic form in FIG. 33.

Figure 33:
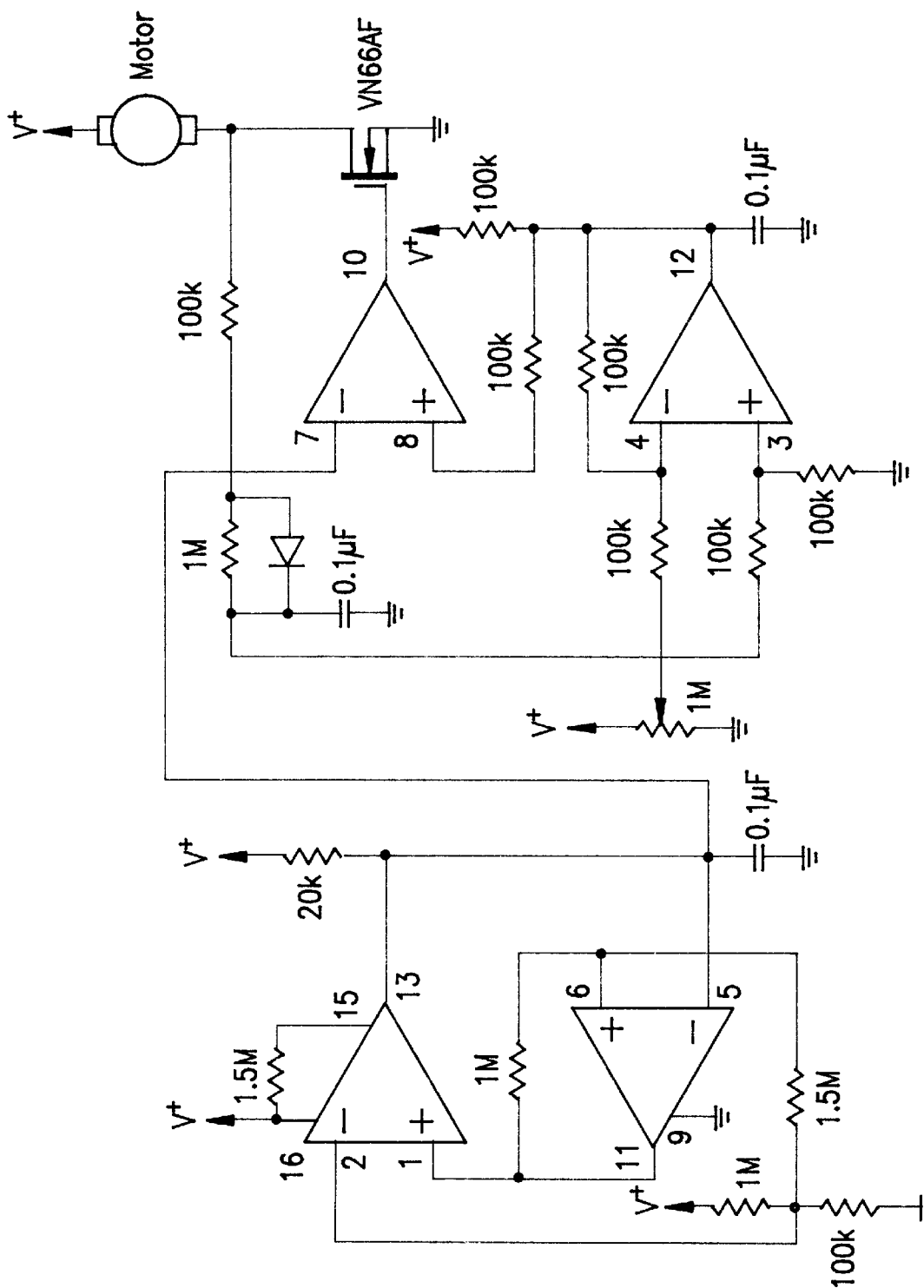
FIG. 33 is a schematic diagram of an electronic variable speed DC motor control.
Figure 34:
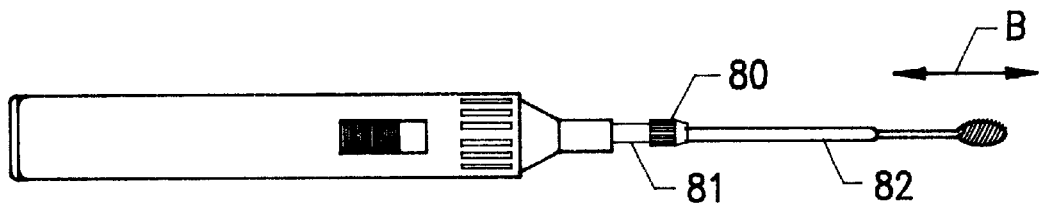
FIG. 34 is a plan view of a third embodiment of a surgical file apparatus according to the present invention.
Figure 35:
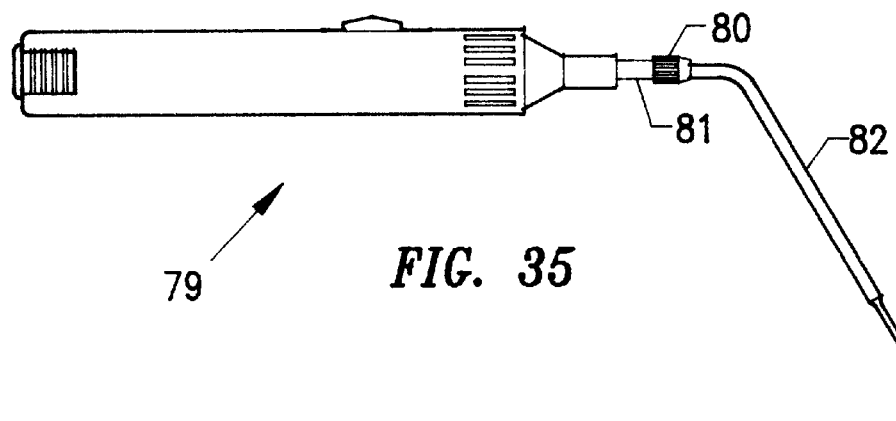
FIG. 35 is a front view of the third embodiment.
Figure 36:
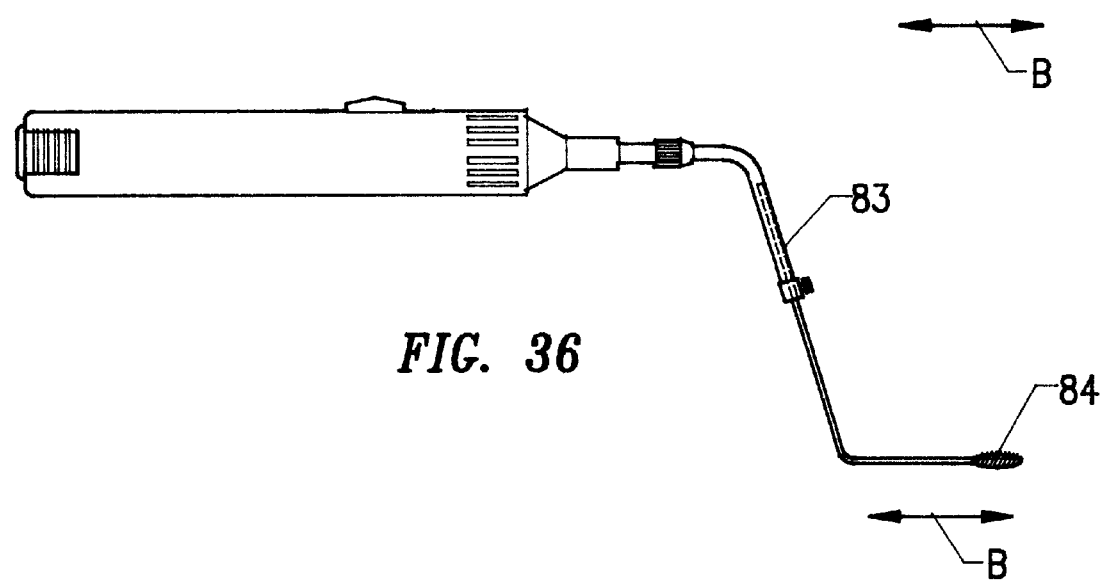
FIG. 36 is a plan view of a fourth embodiment of a surgical file apparatus according to the present invention.

With reference to FIG. 33, the more efficient approach is to chop the dc and obtain a variation in armature voltage by varying the duration of the "ON" time of the chopper. The principle of operation is an adaptation of the pulse-width modulation concept used in switching power supplies.

The four op amps are part of a single IC chip. The circuit is comprised of the IC op amp chip, a power MOSFET and a few passive components. Speed sampling is accomplished by monitoring the counter EMF (electromotive force) of the motor. Monitoring is done by the lower right-hand op-amp through the 100 k ohm resistor connected to the motor's armature. Sensing takes place when the power MOSFET is turned off.

The upper right-hand op amp is the PWM modulator. It delivers a rectangular wave to the motor, with a duty cycle determined by the dc voltage level applied to its non-inverting terminal by the previously described sense op amp amplifier, i.e. the lower right-hand op amp. The inverting input terminal of the PWM receives a triangular wave from an oscillator comprising the two left-hand op amps 74. Thus, the PWM is an op amp fed by a variable dc voltage and a triangular wave. Speed control occurs because of the change in the average value of armature current which can be changed by adjusting the 1-megohm potentiometer 75 associated with the sensing op amp amplifier. Motor speed is maintained constant for any adjusted speed, even though there are variations in applied motor voltage, in mechanical loading of the motor, or motor temperature.

Figure 5:
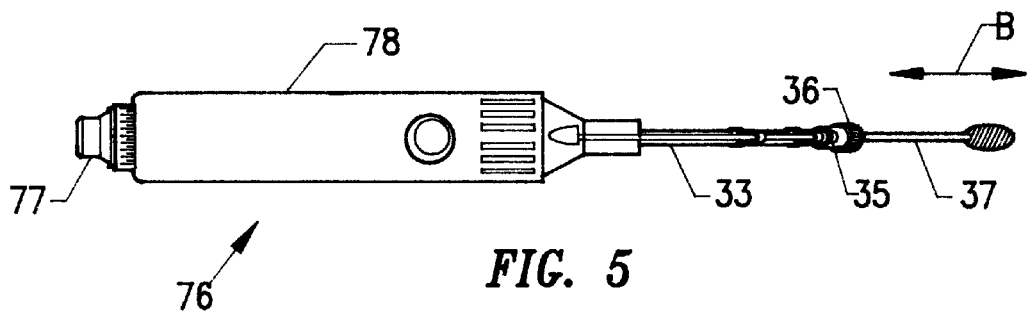
FIG. 5 is a plan view of a second embodiment having an AC power source.
Figure 6:
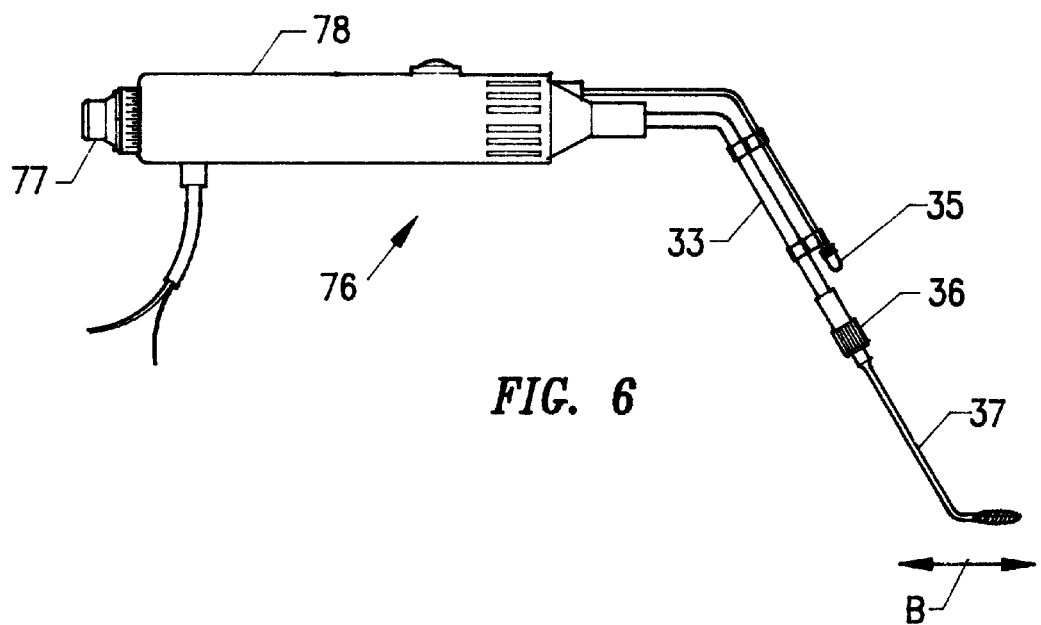
FIG. 6 is a front view of the second embodiment.
Figures 7, 8, 9:
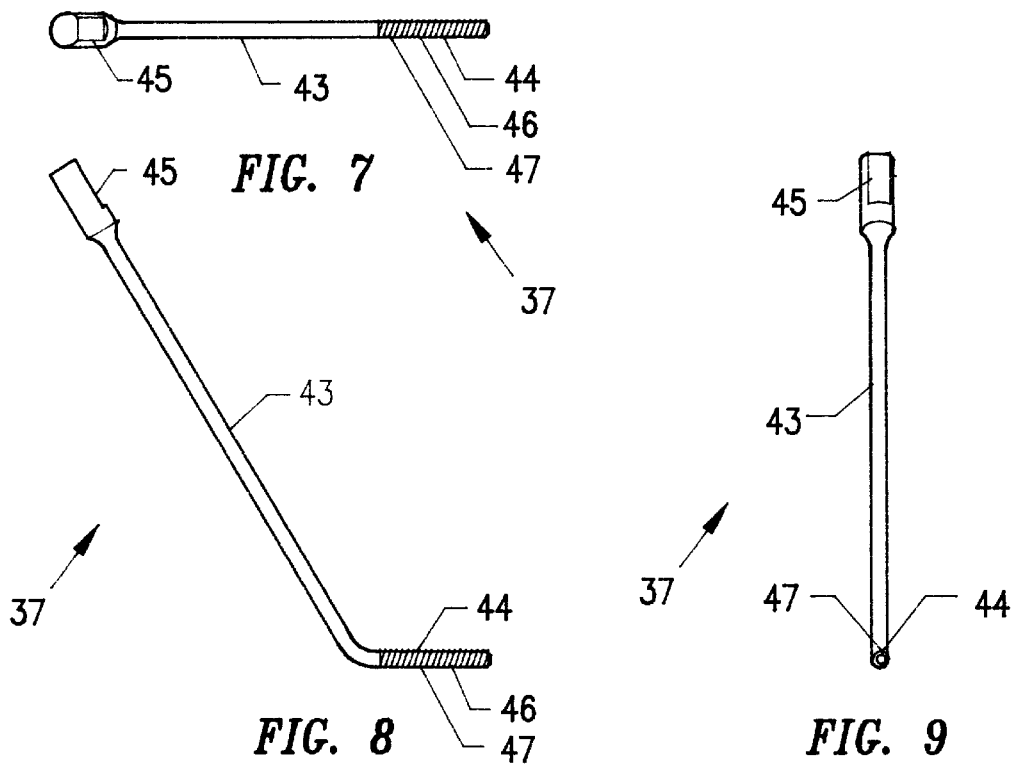
FIG. 7 is an enlarged plan view of an offset round file.
FIG. 8 is an enlarged front view of the offset round file.
FIG. 9 is an enlarged left end view of the offset round file.
Figures 10, 11, 12, 13, 14:
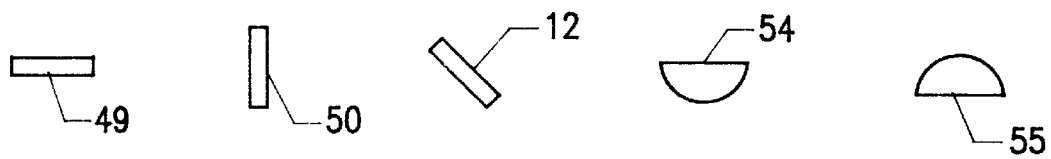
FIG. 10 is an enlarged cross-section view of an offset rectangular file.
FIG. 11 is an enlarged cross-section view of a second offset rectangular file.
FIG. 12 is an enlarged cross-section view of a third offset rectangular file.
FIG. 13 is an enlarged cross-section view of an offset half round file.
FIG. 14 is an enlarged cross-section view of a second offset half round file.
Figures 15, 16, 17, 18, 19:
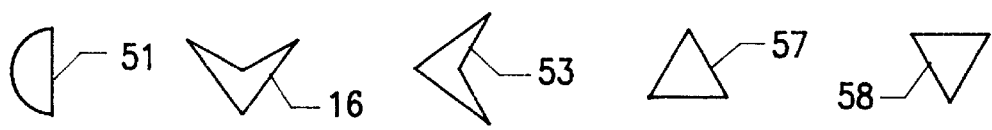
FIG. 15 is an enlarged cross-section view of a third offset half round file.
FIG. 16 is an enlarged cross-section view of an offset "V" file.
FIG. 17 is an enlarged cross-section view of a second offset "V" file.
FIG. 18 is an enlarged cross-section view of a triangular file.
FIG. 19 is an enlarged cross-section view of a second triangular file.

In a second aspect of the invention 76, shown in FIGS. 5 and 6, the surgical file is powered by an AC source. A rotary control 77 on a rear portion of the housing 78 is used for selectively changing the rate at which the offset file 37 reciprocates.

Referring now to FIGS. 26 and 27, an alternate embodiment 79 is illustrated therein, wherein a coupling 80 for optional files is mounted on an end portion of a short reciprocating shaft 81 which extends outwardly from the motor and drive 39. One benefit of this embodiment 79, is that files can be provided with optional angles of upward extending arms 82. In FIG. 28 a telescopic file arm is depicted which allows the amount of offset between the motor 39 and offset file 84 to be varied.

It will be apparent from the preceding description that the objects of the invention are efficiently attained. Since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

We claim:

1. A motor driven reciprocating surgical file apparatus for trimming and shaping hard body materials such as bone and cartilage comprising: a housing; a motor and drive unit mounted within said housing, said motor and drive unit having a reciprocating output shaft, said reciprocating output shaft extending outwardly from said motor and drive unit; a power supply for said motor and drive unit; a coupling at a distal end portion of said outward extending output shaft for receiving an upward extending arm of an offset file; and an offset file, said offset file having a slender elongated upward extending file arm portion for engaging said coupling and a lower adjoining file portion, said lower adjoining file portion having a plurality of teeth for shaping and trimming hard body materials in a direction which is substantially parallel to an axis of said outward extending upper portion of said motor and drive unit shaft when said offset file is mounted in said coupling.

2. The surgical file apparatus recited in claim 1 wherein said file portion is a round file in cross-section.

3. The surgical file apparatus recited in claim 1 wherein said file portion is a square file in cross-section.

4. The surgical file apparatus recited in claim 1 wherein said file portion is a rectangular file in cross-section.

5. The surgical file apparatus recited in claim 1 wherein said file portion is a "V-shaped" file in cross-section.

6. The surgical file apparatus recited in claim 1 wherein said file portion is a "Y-shaped" file in cross-section.

7. The surgical file apparatus recited in claim 1 wherein said file portion is a half round file in cross-section.

8. The surgical file apparatus recited in claim 1 wherein said file portion is a concave-convex file in cross-section.

9. The surgical file apparatus recited in claim 1 wherein said file portion is an asymmetrical file in cross-section.

10. The surgical file apparatus recited in claim 1 wherein said file portion is a tapered file.

11. The surgical file apparatus recited in claim 1 wherein said file portion is a rough course file.

12. The surgical file apparatus recited in claim 1 wherein said file portion is a fine file.

13. The surgical file apparatus recited in claim 1 wherein said file portion is a rasp file.

14. The surgical file apparatus recited in claim 1 wherein said power supply is a battery.

15. The surgical file apparatus recited in claim 1 wherein said power supply is an AC power supply.

16. The surgical file apparatus recited in claim 1 further comprising an electronic control means for selectively changing the rate of reciprocation of said offset file.

17. The surgical file apparatus recited in claim 15 wherein said electronic control means comprises an electronic circuit for obtaining a variation in an armature voltage of said motor by.

18. The surgical file apparatus recited in claim 1 further comprising a means for illuminating said lower adjoining portion of said file.

19. A motor driven reciprocating surgical file apparatus for trimming and shaping hard body materials such as bone and cartilage comprising: a motor and drive unit having a reciprocating output shaft; an offset file connected to said reciprocating output shaft of said motor and drive unit, said offset file having an upward extending arm portion extending from said output shaft and an adjoining lower portion, said lower portion being offset from said motor and drive unit and having a plurality of cutting portions for trimming and shaping said hard body materials in the direction of said reciprocating output shaft of said motor and drive unit.

20. A motor driven reciprocating surgical file apparatus for trimming and shaping hard body materials such as bone and cartilage comprising: a motor and drive unit having a reciprocating output shaft, said reciprocating output shaft having an upper portion extending outwardly from said motor and drive unit and an adjoining lower portion extending downwardly from said upper portion; a coupling attached to a lower distal end portion of said lower portion of said motor and drive unit output shaft for receiving an upper end portion of a detachable offset file; and a detachable offset file having an upper extending arm portion connected to said coupling and an adjoining lower portion, said lower portion of said detachable offset file having a plurality of teeth for trimming hard body materials in the same reciprocating direction as said motor and drive unit output shaft.

21. A motor driven reciprocating surgical file apparatus for trimming and shaping hard body materials such as bone and cartilage comprising: a motor and drive unit having a reciprocating output shaft; a coupling attached to a distal end portion of said output shaft; a detachable offset file connected to said coupling, said offset file having an upward extending arm portion and an adjoining lower file portion.

22. The surgical file apparatus recited in claim 21 wherein said upward extending arm portion of said offset file is a telescoping arm portion.

23. A method for trimming and shaping hard body materials such as bones and cartilage comprising the steps of connecting a detachable offset file having an upper portion extending outwardly from a drive unit and a lower portion offset from said drive unit; inserting the lower portion into a surgical site; engaging said lower file portion with a hard body material; reciprocating said file portion with a motor and the drive unit to trim and/or shape said hard body material.

24. The method as recited in claim 23 further comprising the steps of replacing said offset file with a second offset file; engaging a lower file portion of said second offset file with said hard body material; reciprocating the lower file portion of said second offset file to further trim and/or shape said hard body material.

* * * * *

UNITED STATES PATENT AND TRADEMARK OFFICE
CERTIFICATE OF CORRECTION

PATENT NO. : 6,048,345
DATED : April 11, 2000
INVENTOR(S) : Joseph J. Berke and Charles T. Michael It is certified that error appears in the above-indentified patent and that said Letters Patent is hereby corrected as shown below:

Column 4, line 49, after "of FIG.", insert --20--

Column 5, line 16, change "FIG. 33" to --FIG. 25--

Column 5, line 17, change "FIG. 33" to --FIG. 25--

Column 6, line 41, change "course" to --coarse--

Column 6, line 56, delete --by--

Signed and Sealed this

Twentieth Day of February, 2001

Attest:

NICHOLAS P. GODICI

Attesting Officer

Acting Director of the United States Patent and Trademark Office